(12) United States Patent
Villareal et al.

(10) Patent No.: US 12,318,277 B2
(45) Date of Patent: *Jun. 3, 2025

(54) APPARATUS AND METHODS FOR RETRIEVING A FOREIGN BODY FROM A VASCULATURE

(71) Applicant: AVANTEC VASCULAR CORPORATION, Sunnyvale, CA (US)

(72) Inventors: Plaridel Villareal, Sunnyvale, CA (US); Nicholas DeBeer, Sunnyvale, CA (US); Frank Becking, Sunnyvale, CA (US); Karl Halden, Sunnyvale, CA (US); Teresa Ruvalcaba, Sunnyvale, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/535,668

(22) Filed: Dec. 11, 2023

(65) Prior Publication Data

US 2024/0108449 A1 Apr. 4, 2024

Related U.S. Application Data

(63) Continuation of application No. 17/096,455, filed on Nov. 12, 2020, now Pat. No. 11,903,810, which is a
(Continued)

(51) Int. Cl.
*A61F 2/01* (2006.01)
*A61F 2/95* (2013.01)

(52) U.S. Cl.
CPC ............. *A61F 2/0105* (2020.05); *A61F 2/01* (2013.01); *A61F 2/011* (2020.05);
(Continued)

(58) Field of Classification Search
CPC .... A61F 2/011; A61F 2/22031; A61F 2/2436; A61F 2/50; A61F 2017/00623;
(Continued)

(56) References Cited

U.S. PATENT DOCUMENTS 3,952,737 A 4/1976 Lipfert et al.
4,085,743 A 4/1978 Yoon
(Continued)

FOREIGN PATENT DOCUMENTS

EP 1172073 A1 1/2002
JP H 10-509623 A 9/1998
(Continued)

OTHER PUBLICATIONS

U.S. Appl. No. 62/091,433, Villareal, et al., filed Dec. 12, 2014.
(Continued)

*Primary Examiner* — Martin T Ton
(74) *Attorney, Agent, or Firm* — Brian S. Boyer; SYNDICATED LAW, PC

(57) ABSTRACT

Apparatus and methods for retrieving a foreign body from a vasculature are provided. The devices can be Funnel-trap type retrieval devices. The devices can include a compressible support member extending from the distal end of an elongate shaft, the compressible support member having an expanded configuration, a compressed configuration, a plurality of independent elongate support elements that have a memory for the funnel-shaped expanded configuration, and a cover material that covers the compressible support member and forms a pocket configured for capturing the foreign body in the interior of the compressible support member.

20 Claims, 9 Drawing Sheets

Related U.S. Application Data continuation of application No. 15/969,353, filed on May 2, 2018, now Pat. No. 10,856,962, which is a continuation of application No. 14/965,500, filed on Dec. 10, 2015, now abandoned.

(60) Provisional application No. 62/091,433, filed on Dec. 12, 2014.

(52) U.S. Cl.
CPC . *A61F 2002/016* (2013.01); *A61F 2002/9528* (2013.01); *A61F 2210/0014* (2013.01); *A61F 2230/0041* (2013.01); *A61F 2230/005* (2013.01); *A61F 2230/0067* (2013.01); *A61M 2207/00* (2013.01)

(58) Field of Classification Search
CPC .. A61F 2017/22031; A61F 2017/22035; A61F 2017/2215; A61F 2002/9528
See application file for complete search history.

(56) References Cited

U.S. PATENT DOCUMENTS

| | | | |
|---|---|---|---|
| 4,174,715 A | 11/1979 | Hasson | |
| 4,467,802 A | 8/1984 | Maslanka | |
| 4,611,594 A | 9/1986 | Grayhack et al. | |
| 4,655,219 A | 4/1987 | Petruzzi | |
| 4,723,936 A | 2/1988 | Buchbinder et al. | |
| 4,873,978 A | 10/1989 | Ginsburg | |
| 4,960,411 A | 10/1990 | Buchbinder | |
| 5,074,845 A | 3/1991 | Miraki et al. | |
| 5,011,488 A | 4/1991 | Ginsburg | |
| 5,041,093 A | 8/1991 | Chu | |
| 5,098,440 A | 3/1992 | Hillstead | |
| 5,102,415 A | 4/1992 | Guenther et al. | |
| 5,370,647 A | 12/1994 | Graber et al. | |
| 5,549,626 A | 8/1996 | Miller et al. | |
| 5,601,595 A | 2/1997 | Smith | |
| 5,653,684 A | 8/1997 | Laptewicz et al. | |
| 5,662,671 A | 9/1997 | Barbut et al. | |
| 5,746,251 A | 5/1998 | Bullard | |
| 5,782,747 A | 7/1998 | Zimmon | |
| 5,800,457 A | 9/1998 | Gelbfish | |
| 5,814,064 A | 9/1998 | Daniel et al. | |
| 5,827,324 A | 10/1998 | Cassell et al. | |
| 5,846,251 A * | 12/1998 | Hart | A61B 17/22031 606/127 |
| 5,908,435 A | 6/1999 | Samuels | |
| 5,911,734 A | 6/1999 | Tsugita et al. | |
| 5,944,728 A | 8/1999 | Bates | |
| 5,971,938 A | 10/1999 | Hart et al. | |
| 6,001,118 A | 12/1999 | Daniel et al. | |
| 6,152,946 A | 11/2000 | Broome et al. | |
| 6,156,055 A * | 12/2000 | Ravenscroft | A61B 17/50 606/127 |
| 6,159,230 A | 12/2000 | Samuels | |
| 6,203,561 B1 | 3/2001 | Ramee et al. | |
| 6,210,370 B1 | 4/2001 | Chi-Sing et al. | |
| 6,238,412 B1 | 5/2001 | Dubrul et al. | |
| 6,241,738 B1 | 6/2001 | Dereume | |
| 6,251,092 B1 | 6/2001 | Qin et al. | |
| 6,251,122 B1 | 6/2001 | Tsukernik | |
| 6,264,671 B1 | 7/2001 | Stack et al. | |
| 6,273,900 B1 | 8/2001 | Nott et al. | |
| 6,290,710 B1 | 9/2001 | Cryer et al. | |
| 6,306,163 B1 | 10/2001 | Fitz | |
| 6,336,934 B1 | 1/2002 | Gilson et al. | |
| 6,395,017 B1 | 5/2002 | Dwyer et al. | |
| 6,443,972 B1 | 9/2002 | Bosma et al. | |
| 6,447,531 B1 | 9/2002 | Amplatz | |
| 6,458,151 B1 | 10/2002 | Saltiel | |
| 6,485,501 B1 | 11/2002 | Green | |
| 6,500,182 B2 | 12/2002 | Foster | |
| 6,569,181 B1 | 5/2003 | Burns | |
| 6,569,184 B2 | 5/2003 | Huter | |
| 6,602,271 B2 | 8/2003 | Adams et al. | |
| 6,605,102 B1 | 8/2003 | Mazzocchi et al. | |
| 6,632,236 B2 | 10/2003 | Hogendijk | |
| 6,645,222 B1 | 11/2003 | Parodi et al. | |
| 6,663,652 B2 | 12/2003 | Daniel et al. | |
| 6,679,893 B1 | 1/2004 | Tran | |
| 6,695,813 B1 | 2/2004 | Boyle et al. | |
| 6,699,260 B2 | 3/2004 | Dubrul et al. | |
| 6,702,834 B1 | 3/2004 | Boylan et al. | |
| 6,743,247 B1 | 6/2004 | Levinson et al. | |
| 6,780,196 B2 | 8/2004 | Chin et al. | |
| 6,800,080 B1 | 10/2004 | Bates | |
| 6,833,002 B2 | 12/2004 | Stack et al. | |
| 6,896,690 B1 | 5/2005 | Lambrecht et al. | |
| 6,958,074 B2 | 10/2005 | Russell | |
| 7,211,089 B2 | 5/2007 | Kear et al. | |
| 7,322,989 B2 | 1/2008 | Teague et al. | |
| 7,338,512 B2 | 3/2008 | McGuckin, Jr et al. | |
| 7,377,925 B2 | 5/2008 | Poll | |
| 7,491,210 B2 | 2/2009 | Dubrul et al. | |
| 7,625,390 B2 | 12/2009 | Hendriksen et al. | |
| 7,658,747 B2 | 2/2010 | Forde et al. | |
| 7,731,723 B2 | 6/2010 | Kear et al. | |
| 7,780,693 B2 | 8/2010 | Brady et al. | |
| 7,780,694 B2 | 8/2010 | Palmer et al. | |
| 7,837,702 B2 | 11/2010 | Bates | |
| 7,993,362 B2 | 8/2011 | Lowe et al. | |
| 8,038,704 B2 | 10/2011 | Sherburne | |
| 8,043,322 B2 | 10/2011 | Hendriksen et al. | |
| 8,163,004 B2 | 4/2012 | Amplatz et al. | |
| 8,202,309 B2 | 6/2012 | Styrc | |
| 8,273,073 B2 | 9/2012 | Levine et al. | |
| 8,298,244 B2 | 10/2012 | Garcia et al. | |
| 8,469,969 B2 | 6/2013 | Kear et al. | |
| 8,469,970 B2 | 6/2013 | Diamant et al. | |
| 8,475,488 B2 | 7/2013 | Cartier et al. | |
| 8,512,401 B2 * | 8/2013 | Murray, III | A61F 2/2436 623/2.11 |
| 8,747,597 B2 | 6/2014 | Rosqueta et al. | |
| 8,795,305 B2 | 8/2014 | Martin et al. | |
| 9,232,956 B2 | 1/2016 | Bonneau et al. | |
| 9,949,816 B2 | 4/2018 | Becking et al. | |
| 10,856,962 B2 | 12/2020 | Villareal et al. | |
| 11,376,028 B1 * | 7/2022 | Saadat | A61B 17/320758 |
| 11,903,810 B2 | 2/2024 | Villareal et al. | |
| 2001/0044595 A1 | 5/2001 | Reydel et al. | |
| 2002/0010476 A1 | 1/2002 | Mulholland et al. | |
| 2002/0062135 A1 | 1/2002 | Mazzocchi et al. | |
| 2002/0068967 A1 | 6/2002 | Drasler et al. | |
| 2002/0169474 A1 | 6/2002 | Kusleika et al. | |
| 2002/0193827 A1 | 12/2002 | McGuckin, Jr. et al. | |
| 2003/0130680 A1 | 7/2003 | Russell | |
| 2003/0176884 A1 | 9/2003 | Berrada et al. | |
| 2003/0187474 A1 | 10/2003 | Keegan et al. | |
| 2004/0049226 A1 | 3/2004 | Keegan et al. | |
| 2004/0073230 A1 | 4/2004 | Mulholland et al. | |
| 2004/0093012 A1 | 5/2004 | Cully et al. | |
| 2004/0138677 A1 | 7/2004 | Little et al. | |
| 2004/0153118 A1 | 8/2004 | Clubb et al. | |
| 2004/0181237 A1 | 9/2004 | Forde et al. | |
| 2004/0199202 A1 | 10/2004 | Dubrul et al. | |
| 2005/0187570 A1 | 2/2005 | Nguyen et al. | |
| 2005/0049576 A1 | 3/2005 | Snell et al. | |
| 2005/0267515 A1 | 5/2005 | Oliva et al. | |
| 2005/0283166 A1 | 6/2005 | Greenhalgh | |
| 2005/0159770 A1 | 7/2005 | Divani et al. | |
| 2005/0182439 A1 | 8/2005 | Lowe | |
| 2005/0234502 A1 | 10/2005 | Gilson et al. | |
| 2005/0251197 A1 | 11/2005 | Hensley et al. | |
| 2006/0020256 A1 | 1/2006 | Bell et al. | |
| 2006/0074410 A1 | 4/2006 | Malecki et al. | |
| 2006/0074446 A1 | 4/2006 | Gilson et al. | |
| 2006/0259119 A1 | 5/2006 | Rucker | |
| 2006/0184193 A1 | 8/2006 | Lowe et al. | |
| 2006/0247572 A1 | 11/2006 | McCartney | |
| 2007/0005101 A1 | 1/2007 | Fahey et al. | |
| 2007/0186933 A1 | 1/2007 | Domingo et al. | |

(56) References Cited

U.S. PATENT DOCUMENTS

| | | |
|---|---|---|
| 2007/0027520 A1 | 2/2007 | Sherburne |
| 2007/0112374 A1 | 5/2007 | Paul, Jr. et al. |
| 2007/0129753 A1 | 6/2007 | Quinn et al. |
| 2007/0149996 A1 | 6/2007 | Coughlin |
| 2007/0162048 A1 | 7/2007 | Quinn et al. |
| 2007/0173884 A1 | 7/2007 | Gilson et al. |
| 2007/0239254 A1 | 10/2007 | Chia et al. |
| 2007/0244504 A1 | 10/2007 | Keegan et al. |
| 2007/0282369 A1 | 12/2007 | Gilson et al. |
| 2008/0065137 A1 | 3/2008 | Boucher et al. |
| 2008/0091223 A1 | 4/2008 | Pokorney et al. |
| 2008/0269774 A1 | 10/2008 | Garcia et al. |
| 2009/0222076 A1 | 3/2009 | Figulla et al. |
| 2009/0248060 A1 | 3/2009 | Schneider et al. |
| 2009/0287291 A1 | 4/2009 | Becking et al. |
| 2009/0182370 A1 | 7/2009 | Volobuyev et al. |
| 2009/0192485 A1 | 7/2009 | Heuser |
| 2009/0198315 A1 | 8/2009 | Boudjemline |
| 2009/0222035 A1 | 9/2009 | Schneiderman |
| 2009/0299393 A1 | 12/2009 | Martin et al. |
| 2010/0030254 A1 | 2/2010 | Chanduszko et al. |
| 2010/0057184 A1 | 3/2010 | Randolph et al. |
| 2010/0312268 A1 | 4/2010 | Belson |
| 2010/0137846 A1 | 6/2010 | Desai et al. |
| 2010/0256669 A1 | 6/2010 | Harris et al. |
| 2010/0331949 A1 | 9/2010 | Habib |
| 2011/0288572 A1 | 1/2011 | Martin |
| 2011/0040321 A1 | 2/2011 | Cartier |
| 2011/0046611 A1 | 2/2011 | Christiansen |
| 2011/0178547 A1 | 3/2011 | Paul, Jr. et al. |
| 2011/0282274 A1 | 3/2011 | Fulton, III et al. |
| 2011/0125180 A1 | 5/2011 | Tripp et al. |
| 2011/0307002 A1 | 6/2011 | Gilson et al. |
| 2012/0010699 A1 | 1/2012 | Vesely |
| 2012/0029607 A1 | 2/2012 | McHugo et al. |
| 2012/0041473 A1 | 2/2012 | Nigon |
| 2012/0089216 A1 | 4/2012 | Rapaport et al. |
| 2012/0123515 A1 | 5/2012 | Hosford et al. |
| 2012/0316638 A1 | 8/2012 | Grad et al. |
| 2013/0053882 A1 | 2/2013 | Hocking et al. |
| 2013/0131690 A1 | 5/2013 | Nagl et al. |
| 2013/0184738 A1 | 7/2013 | Laroya et al. |
| 2013/0197567 A1 | 8/2013 | Brady et al. |
| 2013/0253573 A1 | 9/2013 | Agnew |
| 2013/0267848 A1 | 10/2013 | Fearnot et al. |
| 2013/0289694 A1 | 10/2013 | Sherburne |
| 2013/0297010 A1 | 11/2013 | Bishop et al. |
| 2013/0317589 A1 | 11/2013 | Martin et al. |
| 2014/0005712 A1 | 1/2014 | Martin et al. |
| 2014/0024887 A1 | 1/2014 | Ishii et al. |
| 2014/0155930 A1 | 6/2014 | Bennett et al. |
| 2014/0172008 A1 | 6/2014 | McKinnis et al. |
| 2014/0243878 A1 | 8/2014 | Urbanski et al. |
| 2014/0257362 A1 | 9/2014 | Eidenschink |
| 2014/0277089 A1 | 9/2014 | Goode et al. |
| 2014/0309656 A1 | 10/2014 | Gal et al. |
| 2014/0373334 A1 | 12/2014 | Gamarra et al. |
| 2015/0105819 A1 | 4/2015 | Becking et al. |
| 2015/0133918 A1 | 5/2015 | Sachar |
| 2015/0351775 A1 | 12/2015 | Fulton, III |
| 2015/0359547 A1* | 12/2015 | Vale ............... A61M 25/0082 606/115 |
| 2015/0366650 A1 | 12/2015 | Zi et al. |
| 2016/0081704 A1 | 3/2016 | Jeon et al. |
| 2016/0095689 A1 | 4/2016 | Becking et al. |
| 2016/0095690 A1 | 4/2016 | Becking et al. |
| 2016/0166370 A1 | 6/2016 | DeBeer et al. |
| 2016/0166372 A1 | 6/2016 | Villareal et al. |
| 2016/0296315 A1 | 10/2016 | Yachia et al. |

FOREIGN PATENT DOCUMENTS

| | | |
|---|---|---|
| JP | 2003-501203 A | 1/2003 |
| JP | 2004-524049 A | 8/2004 |
| JP | 2005-523767 A | 8/2005 |
| JP | 2007-508902 A | 4/2007 |
| JP | 2008-513121 A | 5/2008 |
| JP | 2008-514276 A | 5/2008 |
| JP | 4109422 B2 | 7/2008 |
| JP | 2009-517124 A | 4/2009 |
| JP | 4320142 B2 | 8/2009 |
| JP | 2013-154183 A | 8/2013 |
| KR | 101133157 B1 | 4/2012 |
| WO | WO 00/16846 | 3/2000 |
| WO | WO 2000/056231 | 9/2000 |
| WO | WO 2012/003369 | 1/2012 |
| WO | WO 2012/009675 | 1/2012 |
| WO | WO 2014/172412 | 10/2014 |
| WO | WO 2014/201380 | 12/2014 |

OTHER PUBLICATIONS

Extended European Search Report for 14810754.3, Apr. 20, 2016, Avantec Vascular Corporation—owned by applicant.
Extended European Search Report for 14907807.3, Oct. 18, 2017, Avantec Vascular Corporation—owned by applicant.
Extended European Search Report for 15867562.9, Oct. 18, 2017, Avantec Vascular Corporation—owned by applicant.
Extended European Search Report for 15867928.2, Oct. 18, 2017, Avantec Vascular Corporation—owned by applicant.
Extended European Search Report for 18910402.5, Oct. 17, 2017, Avantec Vascular Corporation—owned by applicant.
Extended European Search Report for 16873911.8, Oct. 17, 2017, Avantec Vascular Corporation—owned by applicant.
Extended European Search Report for 19208256.8, Jun. 17, 2020, Avantec Vascular Corporation—owned by applicant.
PCT/US2014/042343 Published as WO 2014/201380, Dec. 18, 2014, Avantec Vascular Corporation—owned by applicant.
Written opinion and search report for PCT/US2014/042343, Dec. 18, 2014, Avantec Vascular Corporation—owned by applicant.
PCT/US2014/070166 Published as WO 2016/093869, Jun. 16, 2016, Avantec Vascular Corporation—owned by applicant.
PCT/US2015/058898 Published as WO 2015/058898, May 12, 2016, Avantec Vascular Corporation—owned by applicant.
Written opinion and search report for PCT/US2015/058898, May 12, 2016, Avantec Vascular Corporation—owned by applicant.
PCT/US2015/065025, Published as WO 2016/094676, Jun. 16, 2016, Avantec Vascular Corporation—owned by applicant.
Written opinion and search report for PCT/US2015/065025, Jun. 16, 2016, Avantec Vascular Corporation—owned by applicant.
PCT/US2015/065074 Published as WO 2016/094708, Jun. 16, 2016, Avantec Vascular Corporation—owned by applicant.
Written opinion and search report for PCT/US2015/065074, Jun. 16, 2016, Avantec Vascular Corporation—owned by applicant.
PCT/US2015/065102, Jun. 15, 2017, Avantec Vascular Corporation—owned by applicant.
Written opinion and search report for PCT/US2015/065102, Jun. 15, 2017, Avantec Vascular Corporation—owned by applicant.
PCT/US2017/067343, Published as WO 2018/118939, Jun. 28, 2018, Avantec Vascular Corporation—owned by applicant.
Written opinion and search report for PCT/US2017/067343, Jun. 28, 2018, Avantec Vascular Corporation—owned by applicant.

* cited by examiner

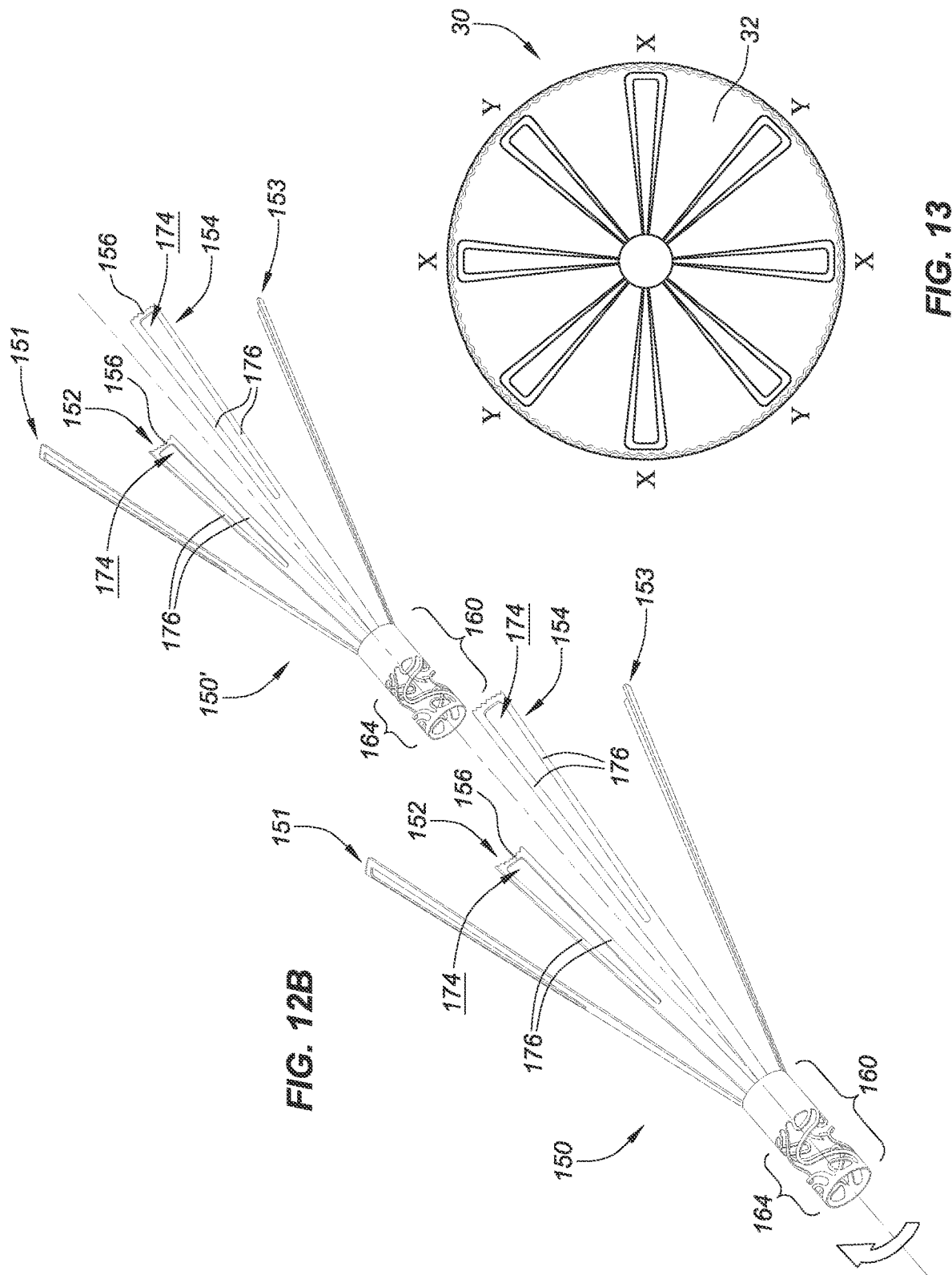

APPARATUS AND METHODS FOR RETRIEVING A FOREIGN BODY FROM A VASCULATURE

RELATED APPLICATIONS

This application is a continuation of U.S. application Ser. No. 17/096,455, filed Nov. 12, 2020, which is a continuation of U.S. application Ser. No. 15/969,353, filed May 2, 2018, which is a continuation of U.S. application Ser. No. 14/965,500, filed Dec. 10, 2015, now abandoned, which claims the benefit of and priority to U.S. Provisional Application Ser. No. 62/091,433 filed Dec. 12, 2014, each of which is herein incorporated by reference in its entirety.

FIELD

The embodiments described herein relate to endovascular temporary Inferior Vena Cava (IVC) filter, other implant or other foreign body retrieval devices or system and methods.

BACKGROUND

Temporary IVC filters are placed much like permanent filters, but are designed so that they may be retrieved in a separate endovascular procedure, generally from a femoral vein or internal jugular vein approach. Most of the currently available temporary filters include a hook-like feature with which they can be captured and received within a catheter or sheath for removal by employing a gooseneck snare or a multi-loop snare.

While retrieval is a simple procedure in principle, difficulty is often encountered capturing a filter's hook with the snare loop(s). Such difficulty is compounded when the filter is tilted or off-kilter in placement. Several filters are designed to avoid such orientation. However, the problem remains common because the device is not anchored into the IVC in a stable fashion. Constant blood flow in addition to blood clots can disorient the filter within the IVC making recapture difficult.

Accordingly, there exists a need for a filter retrieval system with improved ease of use and/or less susceptibility to problems of filter orientation.

SUMMARY

Embodiments hereof meet this need and others as applied to other medical device applications. For IVC filters, the subject systems may be used with a wide variety of filter architectures—existing or otherwise. Accordingly, new filters may be designed for use with the subject retrievers in which fewer design constraints and/or compromises may be required of the filter design. Features of the subject system may be used in connection with existing and/or modified versions of the filters described in any of U.S. Pat. Nos. 3,952,747; 5,601,595; 6,443,972; 7,338,512 and 7,625,390 (all of which patents are incorporated herein by reference in their entireties for any purpose), with commercially available devices including the OPTEASE, GONTHER TULIP, CELECT and OPTION or others.

In the subject embodiments, one or more members are interposed between braid layers defining a funnel trap in the subject device. In one embodiment, the support member may resemble a flower. The support member may comprise a polymer, Nitinol (superelastic at body temperature or below) or other metal or alloy. Especially when the "flower" comprises a thermoplastic material or Nitinol, the "petals" of the so-called flower may be heatset flat at appropriate temperatures as understood by those with skill in the art. In another embodiment, the support members are independent and stabilized between layers of braid as having a hook or "J" shape. These may be originally cut from flat stock or a tube of polymer or metallic material. Such member may be further stabilized by suture loop(s) through or around each such member or body. Advantageously, any knot securing the suture can be positioned within the interior of the funnel trap section of the device. This can be accomplished by tying the knot(s) on the outside and then pivoting the trimmed structure through the braid from which the device is constructed.

In the so-called flower embodiment, a single such member may be used. It may be advantageously cut with four strips, slats, leaflets or petals—collectively, "support elements." More cuts may be made (e.g., with a blade or laser) to define a greater number of elements. However, since it is advantageous for these members to have a large width-to-thickness ratio to avoid lateral displacement when cycling the funnel trap between open and closed (or vice-versa) it may instead be desirable to double-up one flower member with another in a slip or press fit or other telescoping fashion. So paired (or tripled), leaflet or petal width can be maintained while their number is increased.

With this embodiment, the flower also has a shaft. This is typically received over an inner layer of the funnel trap braid. But it can also be positioned inside the inner layer and abut the distal fold of the funnel trap extension. A proximal end of the shaft may be abutted by a heat shrink, glued or fused-on tube to maintain stability without increasing proximal profile. With the flower overlaid by a/the outer braid layer of the funnel trap structure, the entire assembly may be secured by an outer jacket of heat shrink of fused-on polymer layer. Suitable shrink and/or fusing materials include PTFE, FEP, PEBAX, PEEK or others. Adhesive bonding may alternatively be employed.

In the so-called J or hook-shaped embodiment, for proper recapture, it is important that the proximal end of the support members are able to float between the layers. This is so because of the way in which the angles of the braid change during compression. Accordingly, any suture securing the members in position relative to the braid that pass through the members should be located distally. Any proximal stabilization features should be looped around the members to allow translation or slipping.

The former embodiment (i.e., with the flower) may also use lateral stabilization features. However, in this embodiment, the proximal "shaft" of the flower is fixed or pinned with the braid and the braid should slide or translate past the distal end of the leafs or petals. As such, any distal petal stabilization features should be of the loop-type described above in this region.

Other approaches as further shown and described may be employed in support member construction. Examples include laser-cut tubular bodies. Generally, these will be elastic (e.g., as produced in polymer) or superelastic (e.g., as cut from Nitinol hypotube). Such members may be cut in a compressed or collapsed configuration and then plastically or thermally (i.e., as in heatsetting) formed to an expanded shape and then so-assembled with the device embodiment braid. Various optional constructions and construction techniques are detailed below. So-too are different braid layer assembly options.

The subject delivery and/or retrieval devices, kits in which they are included (with and without assembly), methods of use and manufacture (including assembly of the constituent components in vivo or ex vivo) are all included within the scope of the present disclosure. Some aspects of the same are described above, more detailed discussion is presented in connection with the figures below.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 12B is an assembly view of elements as shown in FIG. 12A.

FIG. 13 is an end view of an embodiment constructed with the assembly in FIG. 12B.

DETAILED DESCRIPTION

Various exemplary embodiments are described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the various embodiments. In addition, many modifications may be made to adapt a particular situation, material, composition of matter, process, process act(s) or step(s) to the objective(s), spirit or scope of the present invention. All such modifications are intended to be within the scope of the claims made herein.

Before the present subject matter is described in detail, it is to be understood that this disclosure is not limited to the particular example embodiments described, as such may, of course, vary. It is also to be understood that the terminology used herein is for the purpose of describing particular embodiments only, and is not intended to be limiting, since the scope of the present disclosure will be limited only by the appended claims.

Figure 1A:
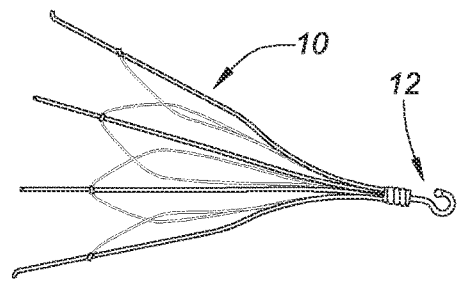
FIGS. 1A and 1B picture IVC filter variations as may be used in the present system.
Figure 1B:
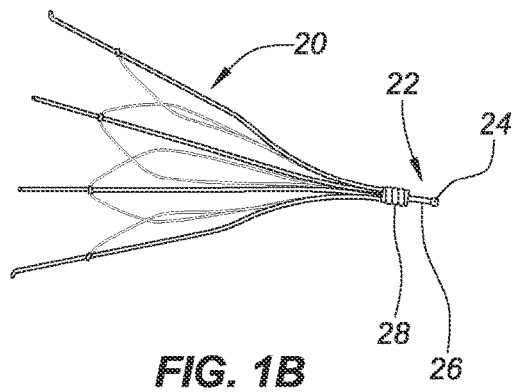
Figure 2:
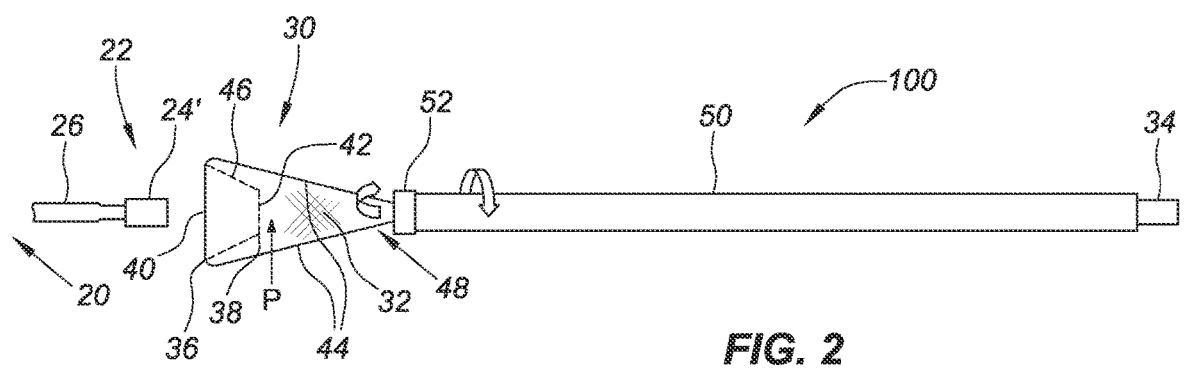
FIG. 2 is a side view of a delivery and/or retrieval system with an end of any type of implantable medical device or foreign body.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description FIG. 1A shows a GÜNTHER TULIP (Cook Medical, Inc.) temporary IVC filter 10 with a hook 12 end interface for retrieval. As shown in FIG. 1B for an IVC filter 20, the hook may be modified or substituted for a nubbin-type interface 22. The nubbin (itself) may comprise a laser-formed or solder-formed protuberance or bump 24 on an extension 26 from a hub 28. Alternatively, as shown in FIG. 2, a/the filter retrieval interface 22 may comprise a band 24' (e.g., a Pt marker band) mounted (e.g., by swaging, welding, gluing, etc.) on a/the extension 26. However, the enlargement is created, the funnel-trap structures described below are adapted to secure that feature for IVC filter retrieval.

FIG. 2 provides an overview of the subject system 100. A funnel-trap structure 30 is shown made of heatset braid material 32. The construction provides a flexible distal extension to an elongate shaft 34. The shaft is received within an elongate sleeve 50 (that may be a commercially available catheter or a custom part of the overall system 100) and may include a distal radiopaque marker band 52.

The braid may comprise Nitinol (preferably that is superelastic at body temperature), CoCr, Stainless Steel or another biocompatible material. It is advantageously braided material incorporating between 72 and 288, or between about 144 and 192 filament "ends" in a 1-over-1, 1-over-2, 2-over-2 or other pattern. With (superelastic) Nitinol, the wire is advantageously between about 0.001 and about 0.003 inches in diameter. In which case, a supple and relatively "smooth" matrix surface is provided from which to construct the flexible funnel-trap architecture shown and described. The value of such a surface is in its atraumatic aspect and/or ability to help guide in IVC filter interface into position for capture even if it is oriented off-angle. Still, other wire size and/or end count in a braid or other construction options are possible as well.

To further assist with recapture, the funnel trap structure 30 may be selectably directable. As indicated by the arrows in FIG. 2, the material from which it is made can be heatset or otherwise configured to provide a bias in an angular direction. The angle of deployment may be selectable or fully straightened by relative position of a core member or obturator (not shown) or by a sleeve or catheter sheath as further described. Further positioning may be achieved by rotating the device as further illustrated. Alternatively, a curved, "L" or "J" shaped wire may be received within a lumen of shaft 34 that can be passed up to and/or through to the inside of the funnel trap structure. Made of superelastic Nitinol (or other) wire, this member can be used to selectively shape or direct the device end.

Other device articulation options for selecting the angular orientation of the funnel-trap portion of the device are possible as well. Any of a variety of steerable or directable catheter-type technologies (reliant on pull-wires or otherwise) can be incorporated in shaft 34 for such purposes. Examples include the mechanisms described in U.S. Pat. Nos. 4,723,936; 4,960,411; 6,251,092 and 8,273,073, each incorporated herein by reference in its entirety, for such description.

The subject "funnel trap" may be generally frusto-conical in shape as shown or otherwise configured. With an outer conical shape (i.e., a triangular shape in cross section as shown) the structure is highly supportive for any necessary or desirable tissue discretion that might need to occur to free an emplaced filter. Moreover, such a shape provides a flexible "waist" section 48 for the directable feature(s) noted above. Still, the device may be bowed outward along its sides or otherwise configured without departing from claimed inventive aspects or variations.

Importantly, the distal rim opening 40 of the structure is larger than the more proximal rim opening 42 to operate in guiding filter engagement feature(s) or enlargement 24/24' into a pocket (P) where it is captured and subsequently locked upon advancing sleeve 50.

Such a pocket is formed between braid walls 44 and bend 38, optionally serving as an abutment feature with an edge or shoulder of nubbin/bump 24/24'. To ensure capture, the sleeve 50 may be advanced fully over trap 30 before withdrawal into a separate catheter. In other words, advancing sleeve 50 over funnel section 30 "closes the trap" and securely captures the implant to be retrieved. Otherwise, the sleeve may be a catheter.

Notably, system 100 may be used identically when capturing a filter 10 with a typical hook end 12. However, the additional bulk/lateral extension of the hook may necessitate use of a relatively larger sleeve or catheter 50. In any case, system use may be visualized fluoroscopically by a physician by way of marker features 24/24' and 52 and/or others as may be conveniently provided.

In the various system architectures, the catheter/pusher shaft and/or sleeve may comprise a simple extrusion (e.g., PTFE, FEP, PEEK, PI, etc.) or may be constructed using conventional catheter construction techniques and include a liner, braid support and outer jacket (not shown), metal hypotube, etc. Further, the filter frame may be constructed using conventional laser cutting and electropolishing techniques and/or be otherwise constructed. In embodiments intended for tracking through a guide/delivery catheter without an incorporated sheath, a loading sheath may be employed. Advantageously, any such loading sheath is splittable. Other typical percutaneous access instruments (such as wires, etc.), valves and other hardware may also be employed in connection with the invention embodiments.

Figure 3:
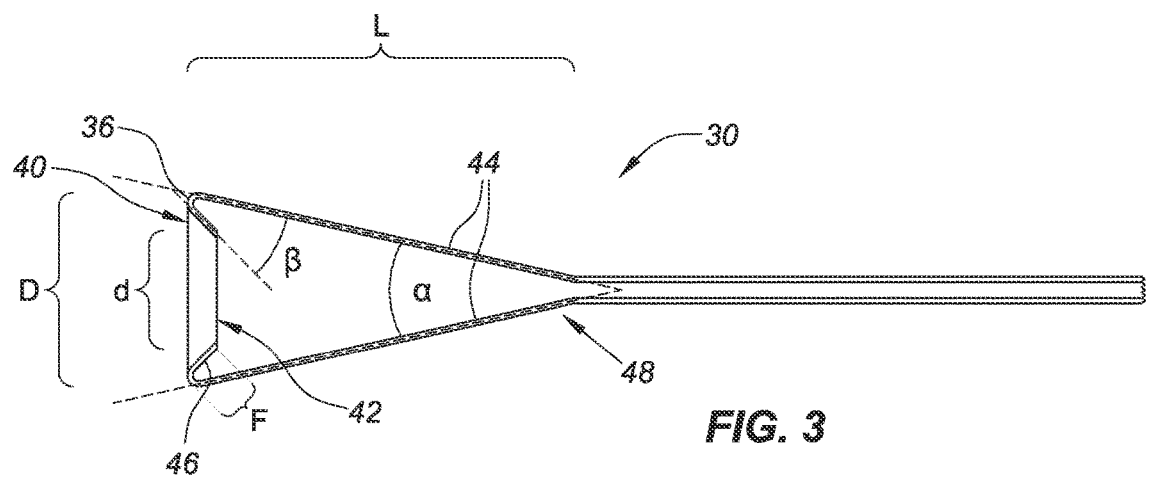
FIG. 3 is a side-sectional view of a converted preform (i.e., a finally shaped funnel section of the subject device) after heatsetting.

The funnel-trap structure 30 may be made as a subassembly and attached to the catheter/pusher shaft. PCT publication PCT/US2014/042343 (WO2014201380) and U.S. patent application Ser. No. 14/569,500, each incorporated by reference in its entirety, detail optional steps in the manufacture of a pre-form for constructing the funnel-trap portion of the final device as shown if FIG. 3.

For IVC filter retrieval, the funnel-trap portion 30 shown may have a diameter (D) from about 5 mm to about 20 mm, or more preferably about 10 to about 15 mm (i.e., size in a range to work within average size human IVCs where such vessels are reported as having a mean diameter of 20 mm within a range of 13 to 30 mm). A length (L) may range from about 10 mm to about 30 mm. An overall cone angle (a) between braid walls 44 may be between about 30 and about 90 degrees. An angle (P) of bend 36 between braid wall 44 and flap 46 may be between about 0 and about 60 degrees and flap length (F) may be between about 1 and about 10 mm in length. Overall, a funnel trap opening diameter (d) may be between about 5 and about 95 percent of diameter (D) depending on the selected combination of the noted variables (i.e., d, D, L, F, α and β). At the lower end of this range, the inner "opening" may be substantially closed such that it must be pushed-open to receive the proximal engagement feature(s) of the implant during retrieval. At the higher end of the range, the flap may lie completely along or in-line with the outer layer(s) of the device. The opening 40 of the funnel trap may be set at 90 degrees relative to a device axis as shown. Otherwise, it may be angled or have a more complex shape as described in connection with FIGS. 9-13 in the above-referenced U.S. patent application Ser. No. 14/569,500, incorporated herein by reference.

Embodiments hereof include a support member or support members set within the funnel trap section or portion of the device. The support member(s) may be interposed between braid layers or set inside the braid layers but interposed between heatset features. FIGS. 4A-4D illustrate an approach to producing the former construction and a method of manufacture.

Figure 4A:
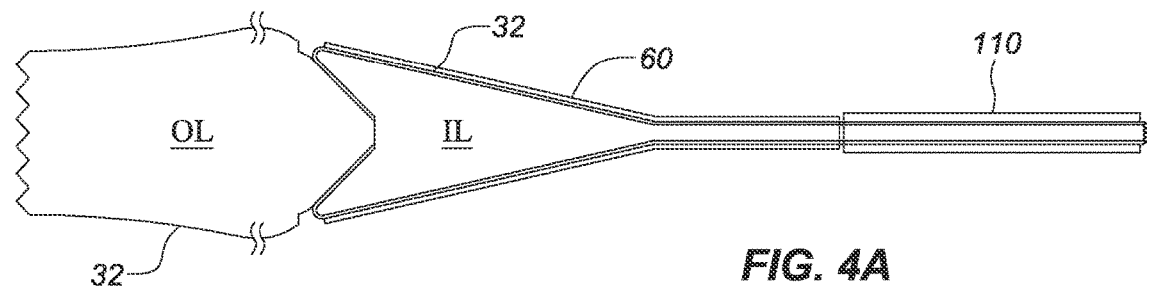
FIGS. 4A-4D are side sectional views illustrating an assembly approach with the subject interposed support member(s).
Figure 4B:
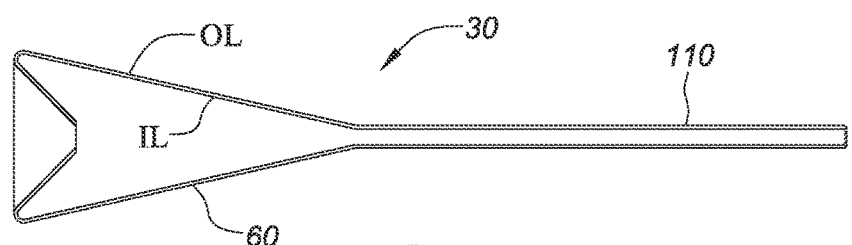
Figure 4C:
Figure 4D:
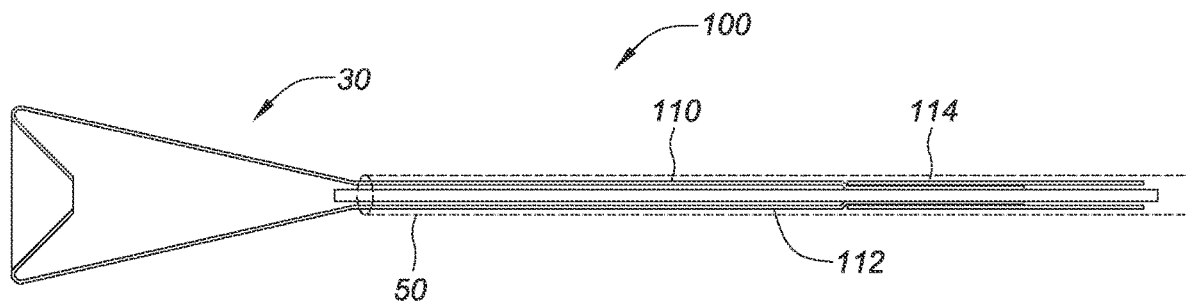

Here, braid 32 is manipulated (in FIG. 4A) flipping an outer layer (OL) over and then back (in FIG. 4B) upon an inner layer (IL) with support member 60 placement and abutment by a locating feature 110 in the form of shrink tubing. The braid layers are re-aligned and shrink tubing 110 reduced in diameter by applying hot air in FIG. 4B. In FIG. 4C, funnel trap structure 30 is mounting on pusher member 34 using another jacketing shrink sleeve 112. In FIG. 4D, a final system assembly is shown with an outer sleeve 50 and optional proximal catheter jacket 114 comprising PTFE shrink or other material.

Figure 5A:
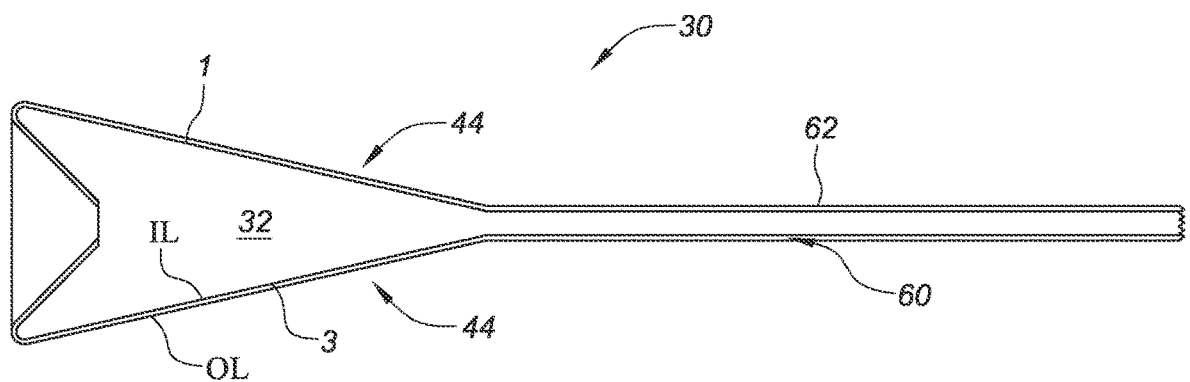
FIGS. 5A-5D are side-sectional views illustrating interposed support member assembly options and features.

FIG. 5A provides an enlarged view of the funnel trap 30 plus support structure 60 shown in FIGS. 4A-4D. Here, the two-layer (IL and OL) construction of the trap 30 formed by heatsetting braid 32 is more apparent. In this cross-section view, two "petals" 1, 3 of the support structure 60 "flower" are shown as well. In this example of a four-petal support member embodiment, petals (which would otherwise be numbered 2 and 4) into an out of the plane of the figure are not show. A section of a cylindrical base or shaft 62 of support structure 30 is, however, shown in cross-section.

Figure 5B:
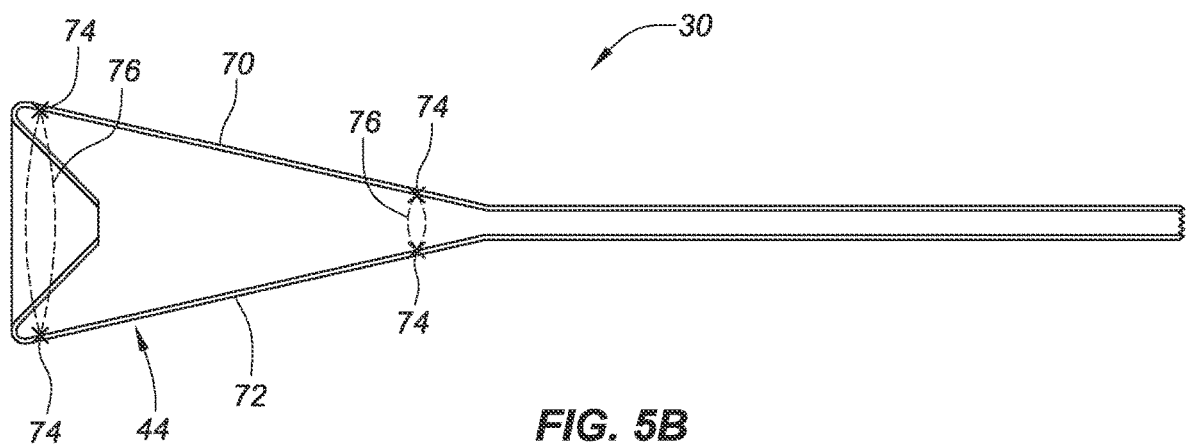

FIG. 5B illustrates another support structure embodiment. Here separate support member 70, 72 "fingers" that are curled or hooked over into "J" shapes are independent of one another and stabilized between layers of braid. (As per the convention in FIG. 5B, the fingers into and out of the page of the cross-section view are not shown.) Such member(s) may be further stabilized by suture loop(s) passing through and/or around each such member or body with knot(s) 74 securing the suture positioned within the interior of the outer walls 44 of the device.

Figure 11:
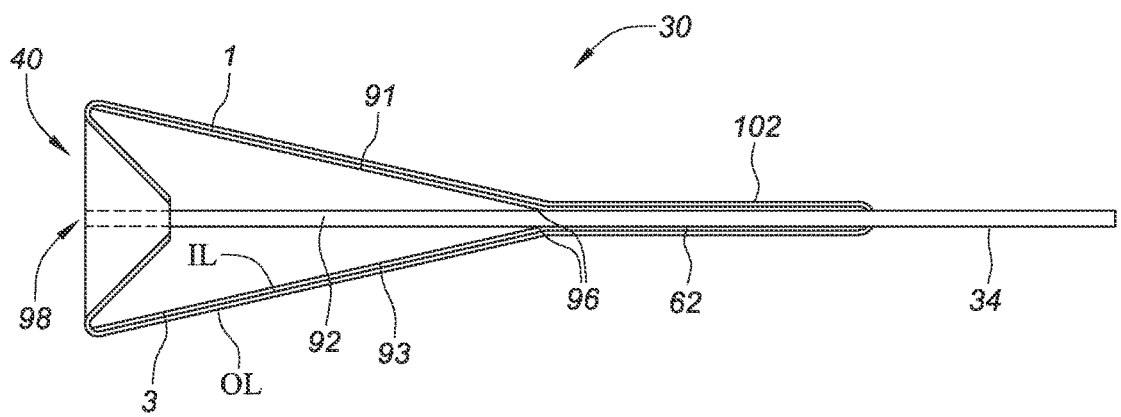
FIG. 11 is a side-sectional view a system including a shaft-based support member.

The sutures may be looped around a single member and interwoven through the braid to form a guide or way. In another approach, the suture is formed in a ring around the circumference of the braid between its layers (an option indicated by the dashed-line loops 76 in the figure) and tied to each member. Such a tie or knotting approach may be facilitated by forming various locator-type through holes in the member 72, 74, etc. as by laser cutting, hypotube drilling or otherwise. An example of such an approach is shown in FIG. 11 (although in different context).

Figure 5C:
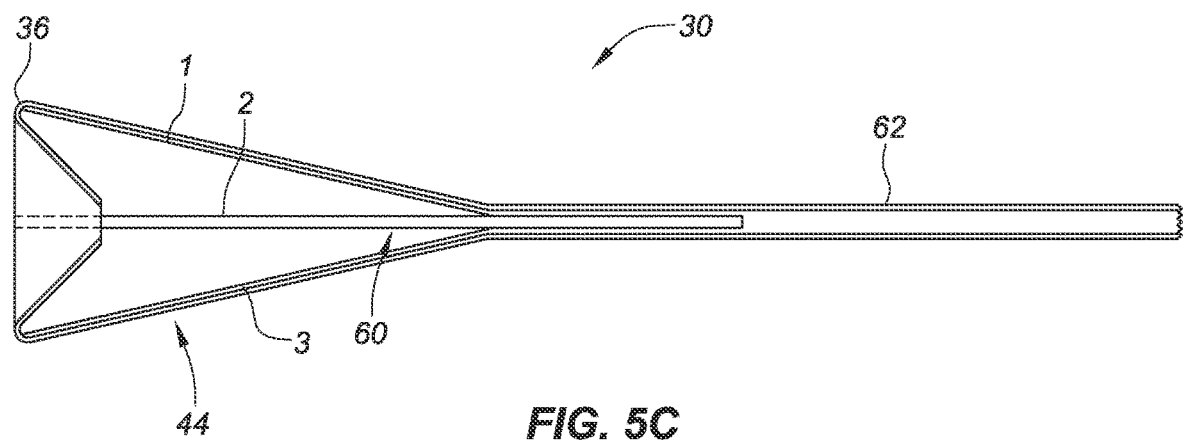

In FIG. 5C, a support member 60 as described in FIG. 5A is placed within the funnel trap structure 30 inside its wall(s) 44. As such, petal number 2 is visible in the figures and extends like the others to adjacent fold 36 to support opening rim 40 (as indicated by dashed line).

Figure 5D:
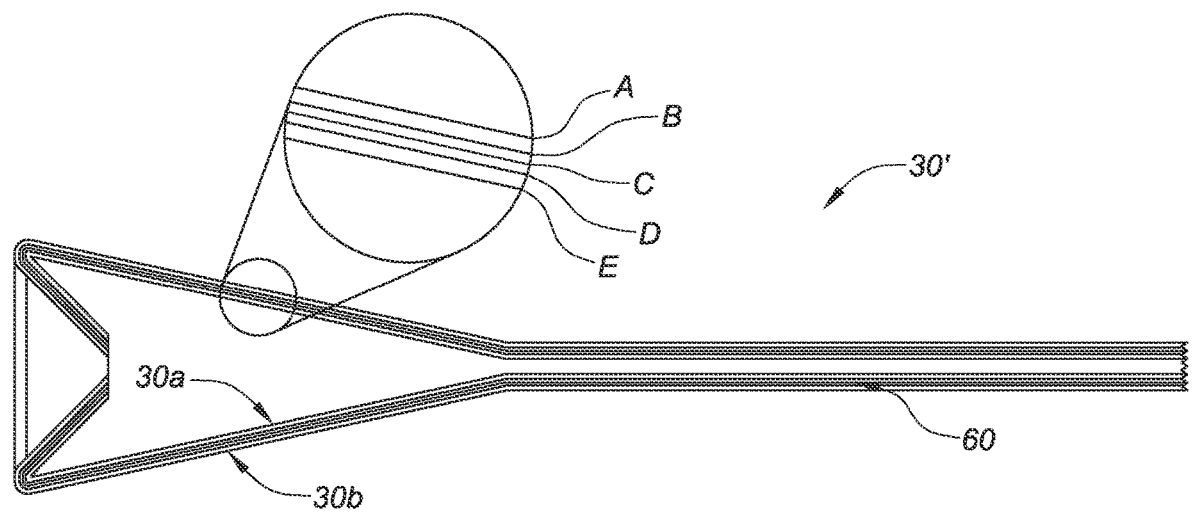

In some ways, the support member placement in FIG. 5D resembles that in FIG. 5A; in other ways it is like that in FIG. 5C. The distinction between the embodiments lies in that FIG. 5D shows a funnel trap construction 30' incorporating two funnel trap preforms 30a and 30b. Thus, it may be said that the FIG. 5D construction takes the approach in FIG. 5C and adds a second, inner funnel trap to the construction. Alternatively, the FIG. 5D construction may be viewed as a doubling-up of layers relative to the FIG. 5A approach.

Regardless, the detail view in FIG. 5D includes five layers (A-D) of material. As shown, layer "C" identifies a/the support member 60 layer. However, other layers combinations are possible, as in an A-C-B-DE combination (i.e., moving the support member 60 or members 72, 74, etc. outward one layer), A-B-D-C-E (i.e., moving the support layer inward one layer) or A-B-D-E-C (i.e., moving the support layer inward two layers). However, the support is received, the doubled-up funnel 30' approach (i.e., with subassemblies 30a plus 30b) may offer benefits when lower braid end counts or smaller diameter wires are desired in a given layer while maintaining overall braid density.

Figure 6A:
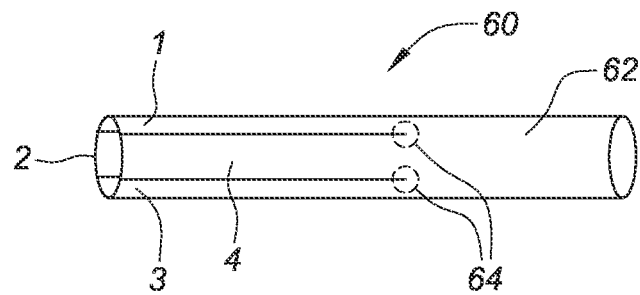
FIG. 6A is a perspective side view one support member in an as-cut or compressed configuration.

FIGS. 6A and 6B and FIGS. 8A and 8B detail methods of manufacture for certain support member embodiments. FIG. 6A is a perspective side view one support member in an as-cut or compressed configuration. In FIG. 6A, a tube (e.g., PET, PTFE or PEEK) is cut with four slits or slots to define a support member 60 four petals 1, 2, 3, 4 leaving an interconnected support base or sleeve 62. The cutting may be done with a blade or laser cutter. Use of a laser will facilitate the addition of optional stress-relief features 64 (dotted line) at the petal junctions as well.

Figure 6B:
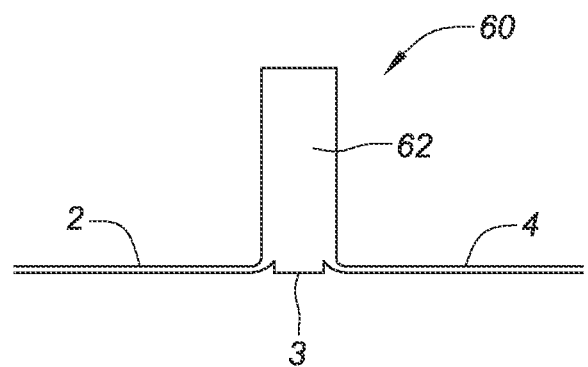
FIG. 6B is a side view of a/the support member heatset in a splayed and flattened configuration.
Figure 7:
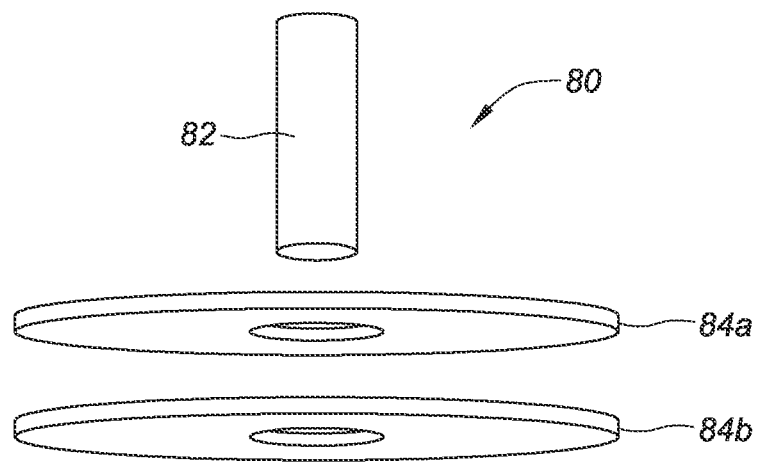
FIG. 7 is a perspective view of tooling for heatsetting a support member as shown in FIG. 6B.

When cut in metal such as Nitinol, the relief features 64 may be necessary. In plastic, they are not. In either case, the body shown in FIG. 6A is advantageously heatset in a splayed-out form as shown in FIG. 6B. This can be accomplished in connection with tooling 80 as illustrated in FIG. 7 and a heatsetting or annealing oven. The tooling may comprise a shaft or rod 82 to center the support member shaft or sleeve 62 and washers 84a, 84b for compressing petals 1-4 flat.

Figure 8A:
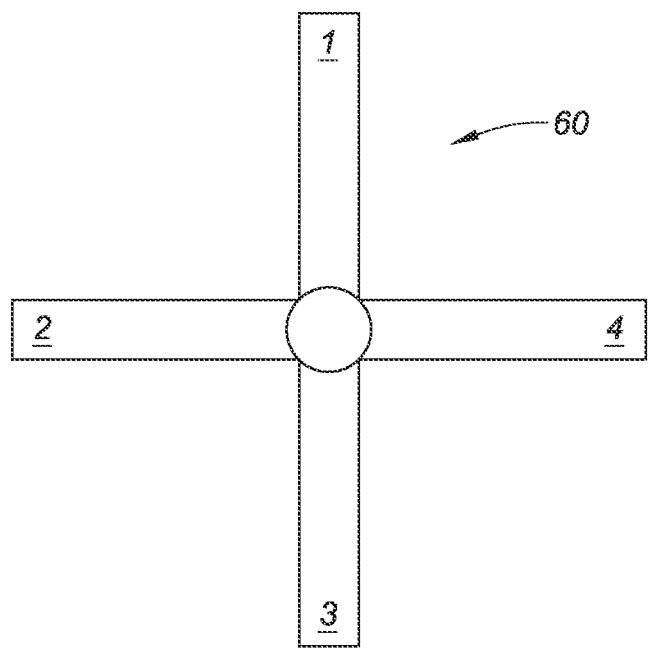
FIG. 8A is a top view of an open support member.
Figure 8B:
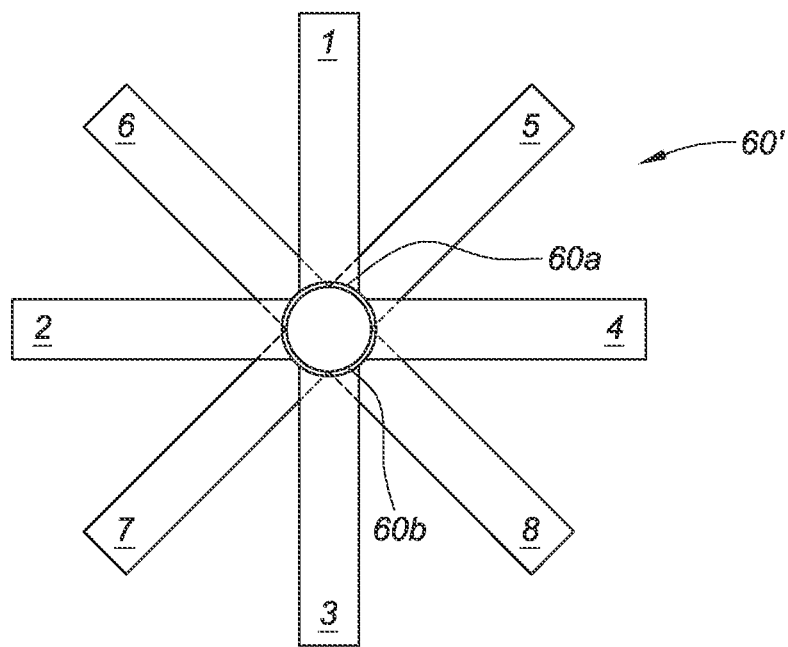
FIG. 8B is a top view of paired support members.

FIG. 8A provides a top view of a support member 60 so-set. With the material heatset open and flat (or set in an approximately conical shape), the structure assists the resiliency of the braid 32 in opening the funnel trap structure 30 upon deployment. FIG. 8B illustrates how a first support member 60a can be nested with a second support member 60b to form a combined support member 60'.

In this case, the nesting doubles the number of support petals. The approach (i.e, nesting of at least two support member sub-assemblies) offers a maximum number of petals, with maximum possible pedal width each (as compared to cutting more petals out of a single tube). The maximized width may be particularly useful in providing lateral stability for the elements when constructed of thin material (e.g., on the order of 0.002 to about 0.005 inches thick) and/or avoiding pushing or poking through the braid the members are intended to support.

Figure 9:
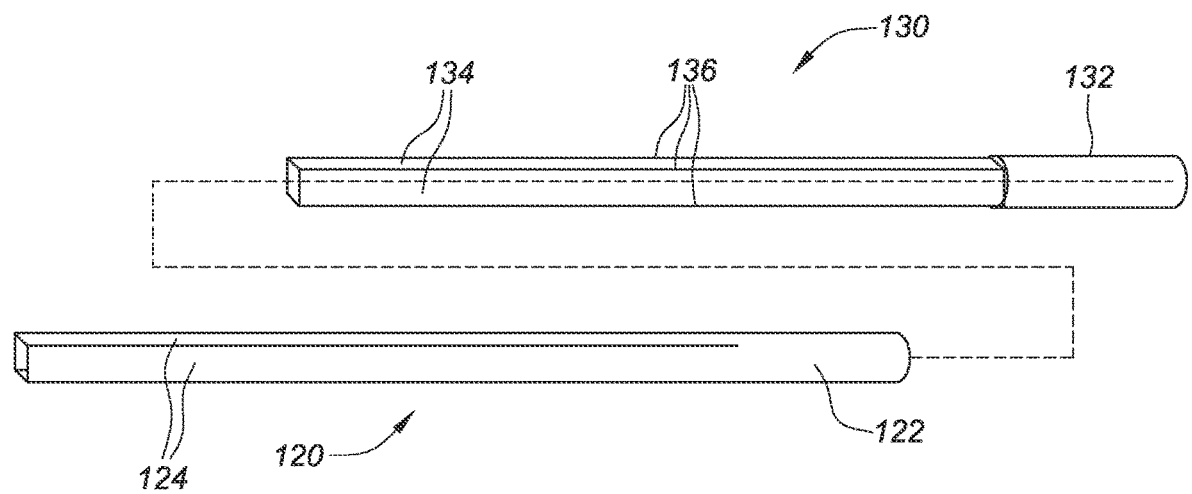
FIG. 9 is an assembly view illustrating support member construction according to heat-shrink material based approach.

FIG. 9 illustrates still another approach to support member construction. Here, a support 120 is constructed using tubing (e.g., PET or PEEK heat shrink) that is heat shrinked or formed onto a mandrel 130. A cylindrical portion 132 of the mandrel provides a round interface portion 122 of the support for mounting to the device shaft 34. Flats 134 on the mandrel result in flat portions or petals 124 in the support. When originally formed by heat shrinking on the mandrel, the petals are connected. However, they are cut with shears, a razor blade or otherwise along squared edges (dashed lines) formed by edges 136 of the mandrel.

One such support may be used in a construct as described above. Otherwise a pair (or more) may be nested concentrically. When stacked or nested, as before, the petals are advantageously offset from one another. A symmetrical offset of 45 degrees is advantageous for support members each including four petals, thus providing a combined structure with eight symmetrically arranged support petals. With a support member formed with three petals to be nested with another to form a final construct with six petals, the offset between each petal is advantageously 60 degrees.

Also, it is possible to plastically deform and set the petals splayed outwards. In a heat-shrink embodiment, it should be done mechanically (i.e., without significant heating), in order to avoid inadvertent (mis)shaping by unintended recovery of the heat shrink tubing. Nevertheless, when two support bodies are employed in a concentric arrangement, they may heat-staked together using a soldering iron tip by cross-wise penetration (or otherwise joined, e.g., by adhesive wicked between the bodies) in order to maintained the desired spacing of petals or for any other reason. The same approach (i.e., heat staking, etc.) may be employed in connection with the FIG. 8B embodiment as well.

Figure 10:
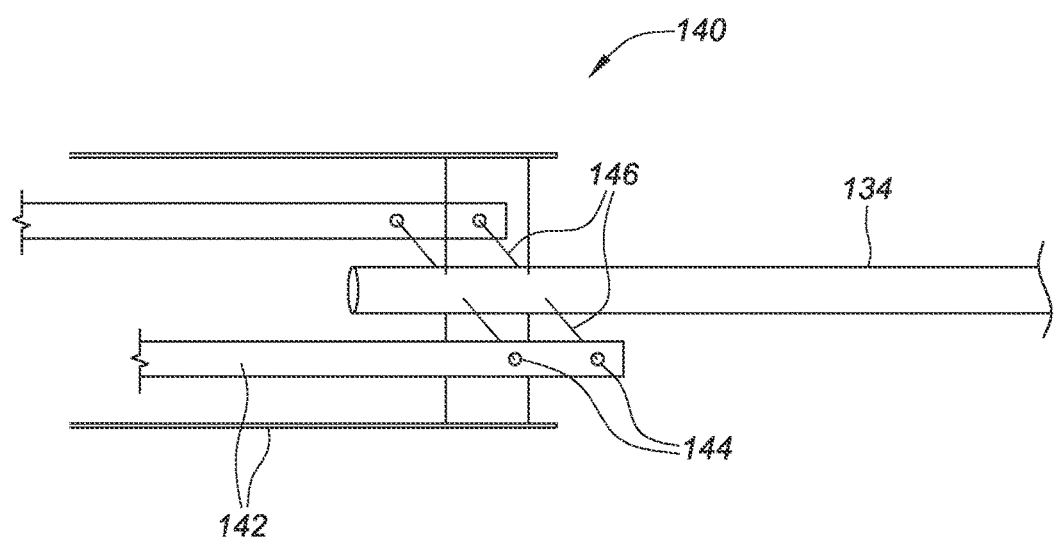
FIG. 10 is another assembly view illustrating support member construction with separate elements.

FIG. 10 illustrates yet another approach to support member construction. Here, a support 140 is constructed either on the end of a shaft 34 (as shown) or as a separate subassembly to be used like other examples above. Either way, the support comprises a plurality of independent extension members 142. These may be formed by die cutting or laser cutting PET, PEEK or another sheet material. And then located as shown onto a support body via guide or eye holes 144. The eye holes may be aligned along axes 146 with wires (wire axes shown) that are removed after affixing the complimentary features (e.g., by gluing, laser welding or fusing by typical catheter constructions techniques or otherwise).

The construct in FIG. 10 may be employed in the support member nesting approach shown in FIG. 11. Alternatively, a tubular shaft 34 can be processed such that its distal end is cut into a support member section 90 with finger or petal extensions 91, 92, 93, etc. therefrom. These extensions can be heatset as described in connection with FIG. 7 or into a conical shape using a matching tool or form. For shape or heatsetting purposes, the shaft advantageously comprises PET or PEEK (as such a selection provides a good compromise in strength, machinability and formability) or Nitinol. The cutting may be performed with a laser and include stress relief features 96 at a junction of the shaft body 34 and extensions. Optional zig-zag end features 98 may also be included in the construction. These zig-zag, square-wave or other such engaging features can assist in maintaining stable position of the support member fingers when the braid of rim opening 40 is compressed and contacting the same. Notably, the same such features may be included in the FIG. 10 and/or FIGS. 12A and 12B embodiment as shown or others as provided herein.

In FIG. 11, the funnel trap embodiment 30 also includes an optional second support member 60 interposed between its braid layers (IL and OL). Notably, the support member 60 fingers 1, 2, etc. are advantageously staggered or interdigitated (as in the manner shown in FIG. 8B) with extensions 5 and 6, etc. coordinated to maximize the number of non-overlapping elements and provide uniform spacing of radial support points for opening rim 40.

In such a system 100, the extension section 30 may be located as shown and bonded with one or more PEBAX (or other thermoplastic material) layers 102 to shaft 34. A laser welding approach is also possible—particularly for embodiments in which all elements are made Nitinol although other materials might be employed to the same effect.

Figure 12A:
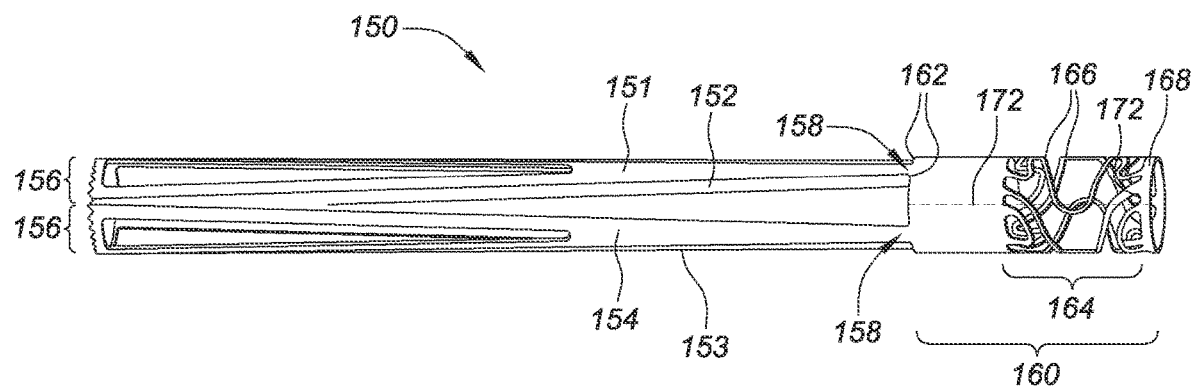
FIG. 12A is a side view of another support member embodiment.

FIG. 12A illustrates a laser cut pattern that may be used for the extension sections of a shaft-cum-support as discussed above. Alternatively, the pattern may define the geometry of a separate support 150 as shown.

In either case, the shape includes a plurality of extensions 151, 152, 153 and 154 in the form of substantially triangular petals, fingers or leaflets. So-configured, the available distal interface area 156 of each member to support the funnel trap braid 32 is maximized in size, while minimizing a waist or flexure section 158 for each petal. The minimized waist provides space for (optionally) radiused stress relief features 160 from a base or stem section 160.

Support member 150 may be so-cut from Nitinol tubing or other material. The cut pattern may include an open stress-relief area 164 comprising a plurality of curved or otherwise configured beams 166 within stem section 160. Such a section will serve as one or more windows for flow-through of bonding material (e.g., thermoplastic PEBAX—or other material—as noted above) without significant increase in stiffness across the entire base 160 of the structure. Alternatively, square or rectangular shaped windows may be provided for bonding. In either case (i.e., with complex, curved windows or rectilinear forms), the windows in each base are advantageously set or "clocked" such that the extensions 151, etc. are spaced apart as desired when the windows are aligned for bonding material flow-through. A proximal rim or band 168 of each support member 150, 150' will prevent pull-out from flow-through bonding approach.

A wide proximal or distal rim or band 170 (i.e., as shown) can—in effect—serve as an integrated radiopaque marker to a/the built-up system. As another option, an inner extent or "frame" portion of one or more aligned windows can be laser welded together to stabilize overall support member 150, 150' position for further assembly processing. Yet another option is to laser or resistance weld proximal or distal rim or band 168, 170 for such purpose(s).

Still further, each rim (or an integrated rim without an intermediate stress-relief section or area 164) may be split as shown, even if cut from cylindrical tubing. A split line 172 may be used for nesting one such tube with another. If the kerf or separation of the split line is wide enough, the base 160 may be compressed and fit inside another tube originally of the same size. Alternatively, a split pair may be employed where one contracts and the other expands.

FIG. 12B illustrates assembly of a pair of support members 150 and 150'. In this example, neither base is split. Rather, the tubes from which the patterns are cut are sized to nest with each other. The base 160 of each body may include a relief pattern 164 configured to match-up when they are set concentrically with each other and offset (e.g., as suggested by the curved arrow so the so-called fingers or petals do not overlap. Alternatively (as shown), the relief patterns may be configured so that they are non-aligned with the petals offset. Such an approach may provide more uniform flexibility.

For use, petal extensions 151, 152, etc. are typically heatset outwardly (as shown) and end interface sections 156 may retain the curvature native to the tube from which they are cut. In which case, any included zig-zag end pattern along with interior relief 174 may provide flexibility when opening or deploying the funnel trap device. Otherwise, the interface sections may be heatset flat (or at least partially flat) for one or both of the support members 150, 150'. In which case, the aforementioned flexibility will assist in fully compressing the device for tracking and/or retrieval. Without such a pattern provided, associated part width or thickness may be altered if so-desired.

With a relief section 174, distal interface 156 (whether zig-zagged, flat or otherwise configured) portions are shown supported by struts 176. Alternatively, relief space 174 may be omitted. Such an embodiment (not shown) may employ a single central strut as part of an overall "T" shaped body.

In any case, FIG. 13 is an end view of a device 100 funnel section 30 with support members 150/150' set within braid material 32. It can be observed through the braid that alternating petals X, Y are wider and narrower, respectively. This is a result of cutting maximum width interface sections 156 from larger and smaller tubing, respectively, for nesting.

With the split-tube approach, the same size interface sections 156 may be provided. However, upon compression, narrower "Y-type" members may compress better (i.e., to their native tube size) offering a reduced device crossing profile. Stated otherwise, excessive dimensional stack-up can be avoided if a mix of X- and Y-type or sized members are provided. Such a consideration may be of use in minimizing locking sleeve 50 size, if used.

VARIATIONS

The subject methods, including methods of use and/or manufacture, may be carried out in any order of the events which is logically possible, as well as any recited order of events. Medical methods may include any of a hospital staff's activities associated with device provision, implant positioning, re-positioning, retrieval and/or release.

Furthermore, where a range of values is provided, it is understood that every intervening value, between the upper and lower limit of that range and any other stated or intervening value in the stated range is encompassed within the invention. Also, it is contemplated that any optional feature of the inventive variations described may be set forth and claimed independently, or in combination with any one or more of the features described herein.

Though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention.

Reference to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity. Accordingly, the breadth of the different inventive embodiments or aspects described herein is not to be limited to the examples provided and/or the subject specification, but rather only by the scope of the issued claim language.

We claim:

1. An apparatus for retrieval of a foreign body, the apparatus comprising:
    an elongate sleeve having a proximal end and a distal end;
    an elongate shaft having a proximal end and a distal end and configured for translating axially in the elongate sleeve;
    a compressible support member extending from the distal end of the elongate shaft and having a proximal end, a distal end, and an interior, and including
        an expanded configuration when translating the compressible support member distally and out of the elongate sleeve to expand the interior;
        a compressed configuration when translating the compressible support member proximally and into the elongate sleeve to compress the interior; and,
        a plurality of independent elongate support elements that are heatset to have a memory for the expanded configuration, and meet at the distal end of the elongate shaft to form a flexible waist, each heatset support element flexing at the flexible waist when translating the collapsible support member into the elongate sleeve for the compressed configuration and out of the elongate sleeve for the expanded configuration;
    and,
    a braid material that
        covers the compressible support member from the proximal end of the compressible support member to the distal end of the compressible support member, the compressible support member supporting the shape of the braid material; and,
        folds over the distal end of the compressible support member and into the interior of the compressible support member as a flap that forms a distal rim opening and a proximal rim opening;
    wherein the distal rim opening, proximal rim opening, and braid material form a pocket for capturing the foreign body in the interior of the compressible support member.

2. The apparatus of claim 1, wherein the proximal rim opening is smaller than the distal rim opening.

3. The apparatus of claim 2, wherein the flap forms a frusto-conical shape of the pocket.

4. The apparatus of claim 1, wherein the plurality of elongate support elements are interposed between layers of the braid material.

5. The apparatus of claim 1, wherein the braid material comprises four layers of braid.

6. The apparatus of claim 1, wherein the proximal end of the support member is coupled to the distal end of the elongate shaft.

7. The apparatus of claim 6, wherein the distal end of the support member has a zig-zag surface to assist in maintaining a stable position of the elongate support elements in contact with the braid during compression of the distal rim opening.

8. The apparatus of claim 1, wherein the support member is directable at the flexible waist.

9. A method of retrieving a foreign body using the apparatus of claim 1, the method comprising:
    positioning the compressible support member in a vasculature of a subject having the foreign body; and,
    retrieving the foreign body from the subject with the apparatus of claim 1.

10. An apparatus for retrieval of a foreign body, the apparatus comprising:
    an elongate shaft;
    a funnel-shaped braid structure having a distal portion folded back inwardly to form a distal opening and a flap; and,
    a plurality of elongate support elements configured to support the funnel-shaped braid structure, wherein each of the plurality of elongate support elements is coupled to the elongate shaft and extends to the distal opening;
    wherein, the plurality of elongate support elements comprise two support members that are concentric bodies that are offset from one another in angular relation to prevent overlap of the respective elongate support elements of each of the two support members in the retrieval of the foreign body.

11. The apparatus of claim 10, wherein the support member is directable where at the flexible waist.

12. An apparatus for retrieval of a foreign body, the apparatus comprising:
    an elongate shaft having a distal end;
    a funnel-shaped braid material having a distal portion folded back inwardly to form a distal opening and a flap; and,
    a plurality of elongate support elements configured to support the funnel-shaped braid material and compress for the delivery or retrieval of the vascular medical device;
    wherein,
    each of the plurality of elongate support elements extends from the distal end of the elongate shaft to the distal opening of the funnel-shaped braid material;
    the plurality of elongate support elements comprise two J-shaped ends and folded inwardly to support the flap of the funnel-shaped braid material; and,
    the proximal ends of the elongate support elements float on the funnel-shaped braid material during the compression of the elongate support elements in the retrieval of the foreign body.

13. The apparatus of claim 12, wherein the support member is directable where at the flexible waist.

14. A funnel trap for retrieval of a foreign body, the funnel trap comprising:
a compressible support member extending from the distal end of an elongate shaft and having a proximal end, a distal end, and an interior, and including
an expanded configuration having a funnel shape;
a compressed configuration; and,
a plurality of independent elongate support elements that have a memory for the funnel-shaped expanded configuration and meet at the distal end of the elongate shaft, each support element flexing at the distal end of the elongate shaft to form the compressed configuration and the funnel-shaped expanded configuration;
and,
a cover material that
covers the compressible support member from the proximal end of the compressible support member to the distal end of the compressible support member, the expanded configuration of the compressible support member supporting the funnel-shape of the cover material; and,
folds over the distal end of the compressible support member and into the interior of the compressible support member to form a pocket having a distal rim opening and a proximal rim opening,
the pocket configured for capturing the foreign body in the interior of the compressible support member.

15. The apparatus of claim 14, wherein the proximal rim opening is smaller than the distal rim opening.

16. The apparatus of claim 15, wherein the proximal rim opening, the distal rim opening, and the cover material form a frusto-conical shape of the pocket.

17. The apparatus of claim 14, wherein the plurality of elongate support elements are interposed between layers of the cover material.

18. The apparatus of claim 14, wherein the proximal end of the support member is coupled to the distal end of the elongate shaft.

19. The apparatus of claim 14, wherein the distal end of the support member has a zig-zag surface to assist in maintaining a stable position of the elongate support elements in contact with the braid during compression of the distal rim opening.

20. A method of retrieving a foreign body using the apparatus of claim 14, the method comprising:
positioning the compressible support member in a vasculature of a subject having the foreign body; and,
retrieving the foreign body from the subject with the apparatus of claim 14.

* * * * *